United States Patent [19]

Jenks

[11] Patent Number: 5,047,190

[45] Date of Patent: Sep. 10, 1991

[54] DIFFERENTIAL SCREW THREAD PRESS FOR PREPARATION OF DISCS FOR SPECTROSCOPIC ANALYSIS

[76] Inventor: Thomas A. Jenks, Box 114, Elbridge, N.Y. 13060

[21] Appl. No.: 542,444

[22] Filed: Jun. 22, 1990

[51] Int. Cl.$^5$ .............................................. B29C 43/02
[52] U.S. Cl. ................................ 264/109; 100/289; 264/112; 425/318; 425/412; 425/423; 425/451.7
[58] Field of Search ................... 264/109, 112, 123; 425/193, 195, 318, 352, 354, 411, 406, 412, 423, 451.7; 100/289

[56] References Cited

U.S. PATENT DOCUMENTS

| 340,979 | 5/1886 | Clapp | 425/354 |
|---|---|---|---|
| 474,496 | 5/1892 | Crossley | 425/352 |
| 1,893,728 | 0/1933 | Bullis | 254/102 |
| 2,149,827 | 3/1939 | Andre | 264/109 |
| 2,771,264 | 0/1956 | Handley | 254/98 |
| 3,052,985 | 9/1962 | Harvey | 100/289 |
| 3,117,615 | 0/1962 | Graven | 72/404 |
| 3,149,375 | 9/1964 | Gehl | 425/352 |
| 3,597,796 | 0/1971 | Ehrlich | 425/195 |
| 4,354,818 | 0/1982 | Morris | 425/405.2 |
| 4,401,614 | 0/1983 | Desantis | 264/109 |

OTHER PUBLICATIONS

Shlomo Gilad, "A Die For Use In The Production of Pellets, Specially For Infra Red Spectrometry", Israeli Patent No. IL30242 (Mar. 30, 1973), Abstract.

*Primary Examiner*—Mary Lynn Theisen
*Attorney, Agent, or Firm*—Wall and Roehrig

[57] ABSTRACT

A differential screw thread press is provided for forming a compacted disc for spectrographic examination purposes by having a pair of opposed threaded bolts in a frame with the bolts having different thread pitches so that they come together as the frame is rotated about the axis of the bolts. The bores for receiving the opposed bolts in the frame are aligned along the same axis and a disc holder is provided for containing the mull to be compacted about the end of one bolt.

10 Claims, 2 Drawing Sheets

DIFFERENTIAL SCREW THREAD PRESS FOR PREPARATION OF DISCS FOR SPECTROSCOPIC ANALYSIS

BACKGROUND OF THE INVENTION

This invention relates to an apparatus for preparing discs of materials for spectroscopic analysis. More particularly, it relates to a press for compacting a quantity of material generally of a relatively transparent salt such as potassium bromide, intimately mixed together with the material to be examined into a compacted mixture which is compressed into a thin fused disc for examination, usually by infrared spectroscopy.

PRIOR ART

Broadly speaking, there have been two types of apparatus used for this purpose in the past. One has been a press in which a ram is forced into a smooth cylinder bore to compact a quantity of material within the bore to a solid disc. This type has required, of course, the use of a press with all the attendant problems of a machine. A second type of press is a screw jack press in which two opposing bolts are tightened against each other within a die body to again compress a quantity of material between the ends of the screws into a fused disc. This type of press has been simple and easy to use, but has had the disadvantage of not producing the high quality smooth surface disc necessary for best results upon spectroscopic analysis. In a dual opposing bolt configuration in order to compact the material placed therebetween, the screws must be rotated relative to each other to cause them to advance together and compact the material. This has, on occasion, caused a roughing or upsetting of the surface of one side or the other of the disc, and has under certain conditions, produced a lower quality disc. Frequently, this type press has also required that a disc holder be used between the bolts As a result, the disc is generally captured by the holder and the holder and disc must be placed in the instrument for spectroscopic analysis. Under certain conditions, this has been a problem when it has been desired to encapsulate a disc before analysis.

OBJECTS AND SUMMARY OF THE INVENTION

Accordingly, it is an object of the present invention to provide an apparatus and method of forming a disc that overcomes the shortcomings of the prior art.

It is another object of the present invention to provide an apparatus for forming compacted discs of material for spectroscopic examination of improved quality and surface finish.

It is a further object of the present invention to provide an apparatus for forming high-quality, smooth surface discs for spectrographic analysis use.

It is a still further object of the present invention to provide an apparatus and method of making discs for spectrographic analysis which includes a material holder in which the disc can be formed and easily removed from the holder without damage.

It is a still further object of the present invention to provide an opposing bolt press in which the ends of the bolts may be forced together to compact material therebetween without rotation of the bolts during the compaction step.

It is yet a further object of the present invention to provide an apparatus for forming discs for spectrographic analysis of the opposed threaded bolt type, in which the surfaces of the bolts contacting the disc do not rotate relative to the surface of the disc during the compacting and compressing action.

It is a still further object of the present invention to provide a differential screw thread press which is easy to handle and operate with ordinary laboratory equipment.

In one embodiment the foregoing is accomplished with a rectangular frame having on opposite sides thereof axially aligned threaded bores in which are positioned a pair of bolts. The pitch of the threads of the bores and bolts are selected to be sufficiently different so as to advance one toward the other when they are held stationary and the frame is rotated about the axis of the bores. This permits formation of a disc without rotating the surface of one bolt against the surface of the material mounted on the surface of the other bolt as the bolts are brought together to compact the material to be tested.

BRIEF DESCRIPTION OF THE DRAWINGS

Further objects of the invention, together with additional features and advantages accruing therefrom will be apparent from the following description and the accompanying drawings, wherein.

DETAILED DESCRIPTION OF A PREFERRED EMBODIMENT

Figure 1:
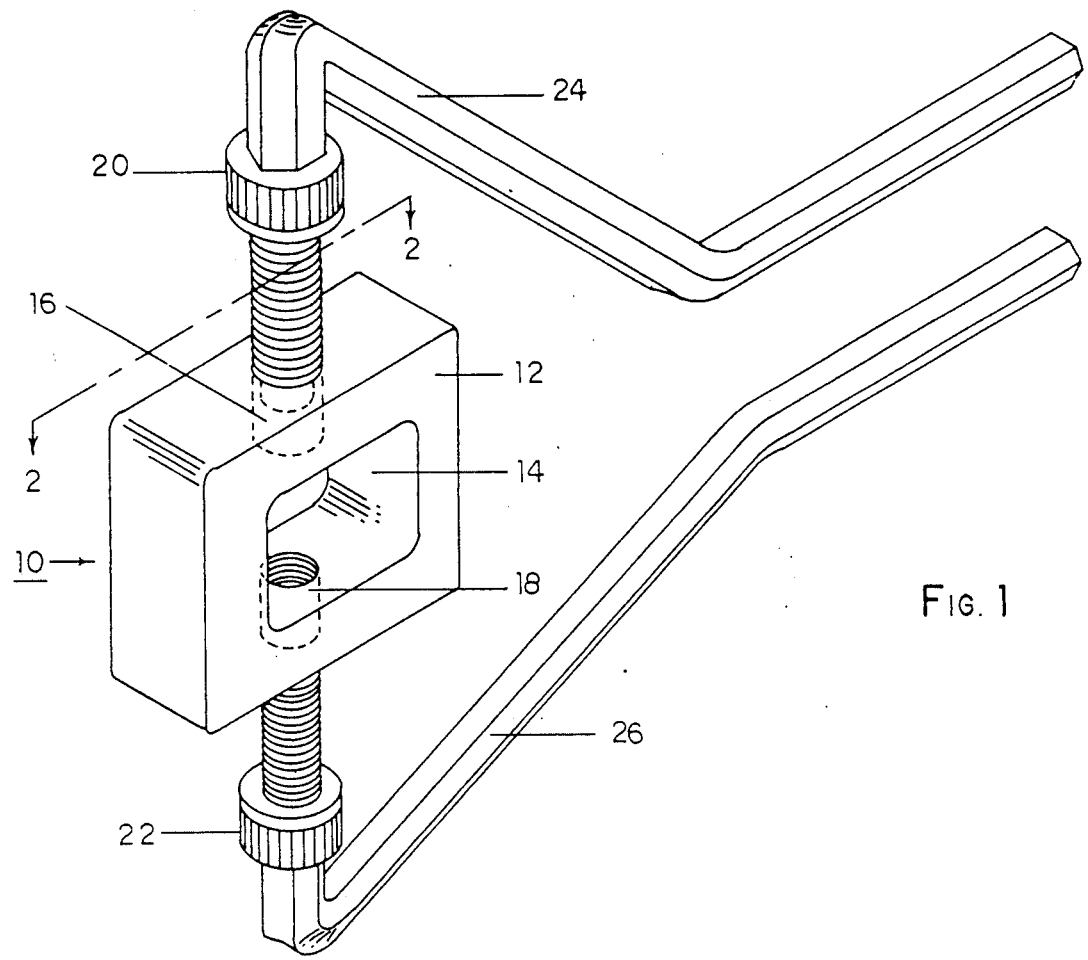
FIG. 1 is a perspective view of the differential screw thread press according to the present invention.

Referring now to FIG. 1, the differential screw press 10 of the present invention consists of an outer rectangular frame or vise member 12, having opposed sides and ends about a central opening 14. The frame 12 has formed therein on opposite sides of the central opening 14 a pair of threaded bores 16 and 18 which are axially aligned one with the other. The frame 12 is made generally of stainless steel with a heavy wall and end sections to be able to receive a bore of sufficient diameter to form a desired size disc for spectroscopic analysis and to have sufficient strength to permit compacting of the material forming the disc into a fused state.

In the embodiment of FIG. 1 the bores are both right hand threaded so that a bolt turned clockwise looking at the head will advance through the frame 12 into opening 14. The bore 16 is chosen to have a different thread pitch than the bore 18 and in one embodiment is chosen with a slightly larger diameter than the bore 18. For instance, in one embodiment, the bore 16 is threaded to receive a 7/16 - 14 Allen Head cap screw and the bore 18 is threaded to receive a ⅜- 24 Allen Head cap screw. It is thus obvious that the difference in the thread pitch from 14 to 24 will cause one screw to move toward the other much more rapidly than the other is withdrawn as the frame is rotated about the axis of the bores with the bolts held stationary. Material placed on one bolt face will thus be compacted as the other bolt advances.

Referring again to FIG. 1, bolts 20 and 22 are positioned within the bores 16 and 18 and generally take the form of a cap screw having an Allen wrench socket in the heads thereof. Special Allen wrenches 24 and 26 are provided to actuate the bolts 20 and 22 and are formed so as to have the ends of the handles adjacent each other for grasping by one hand of the operator of the press when it is desired to hold the two bolts in non-moving alignment.

Figure 2:
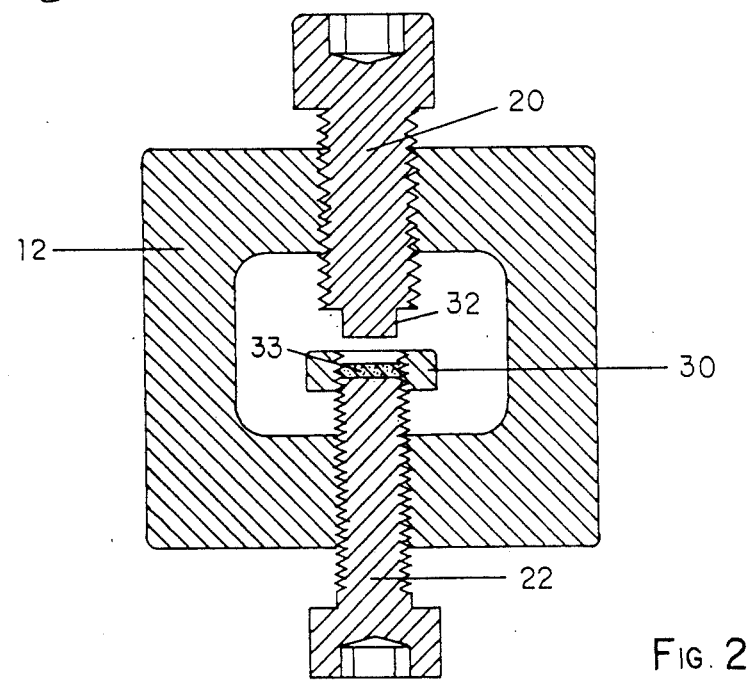
FIG. 2 is a sectional view taken on line 2—2 of FIG. 1.

Referring now to FIG. 2, it can be seen that bolt 22 is threaded to the end and the end of the bolt is cut off perpendicular to the axis thereof. The bolt 20 similarly has the flat end perpendicular to the axis. The free end is turned to form a smooth plunger 32 having a diameter adapted to fit within the disc holder, as will be described herein. The ends of bolts 20 and 20 are highly polished to form a pair of parallel plates for compacting material placed therebetween into fused discs.

As may be seen in FIG. 2, a disc holder 30 is mounted on the bolt 22 and has internal threads corresponding to the threads on the bolt 22 for that purpose. The exterior of the holder 30 usually takes the form of a hexagonal nut so that the disc holder can be held against rotation, as desired. The plunger 32 on the tip of bolt 20 is turned smooth so there are no threads and it is sized to fit snugly within the disc holder 30 so as to be able to compact and compress material placed therein to a solid fused disc 33 without "flash".

In operation, the differential screw thread press 10 is used to form a disc as follows. The bolt 22 which is the lower anvil, is turned into the frame until it extends into the opening 14 approximately halfway. The disc holder 30 is then threaded onto the end of the Allen head cap screw 22 so as to form a cup about the bolt end. The upper anvil bolt 20 is threaded into the bore 16 and a quantity of the mull to be compacted is deposited in the cup formed by the holder 30 and the bolt 22. The anvil bolt 20 is then slowly lowered until it is just touching the material in the disc holder 30. It is sometimes advantageous before bringing the anvil 20 into contact with the material to tap the assembly lightly to get as even a distribution of the material to be compacted as possible. The anvil 20 is the merely brought to finger-tight contact with the mull in the holder 30.

The next step is to insert the Allen wrenches 24 and 26 into their respective bolts and to bring the handle portions together and hold them in one hand or if desired in a vise. The entire frame 12 is then rotated so as to cause the anvil bolt 20 to advance toward the anvil bolt 22. It should be noted that as the frame is rotated, and since the two bores are threaded in the same direction, that the lower bolt 22 will tend to retract while the upper bolt 20 will tend to advance toward the retracting bolt. Because of the difference in the thread pitches of the two, the bolt 20 will advance much more rapidly than the bolt 22 will retract, and thus a strong compressive force can be applied to the mull in the disc holder 30 until the material is fused to form the solid disc 33 for the infrared spectrographic analysis.

After a few minutes when the desired compactness is reached, the frame or vise 12 is rotated in the opposite direction while keeping the anvils 20 and 22 stationary which will cause the upper anvil 20 to move away from the lower anvil 22. Once broken free, the wrenches 24 and 26 can be removed and the anvil 20 retracted by hand. The disc holder 30 then can be unthreaded from the bolt 22 and placed on the sample mount in the spectrograph for spectrum acquisition. The compacting process just described will generally cause the disc 33 formed by compacting the mull to expand slightly into the threads of the disc holder 30 so that it will be securely held within the disc for transport to the analysis instrument and for storing or other purposes. For preparation of the next sample, the anvil members 20 and 22 are cleaned, including the threads, a new disc holder 30 is prepared for installation on anvil 22 and the process repeated. It is thus seen that a very simple and yet efficient device is provided for producing a high-quality disc for spectrographic analysis purposes. Since the surface of bottom bolt 20 and the surface of upper bolt 22 do not rotate relative to each other or to the material held within the holder 30, the upper and lower surface of the disc 32 will be just as smooth and highly polished as the surface of the anvils themselves and thus a very high quality disc is provided for spectrographic analysis use.

Figure 3:
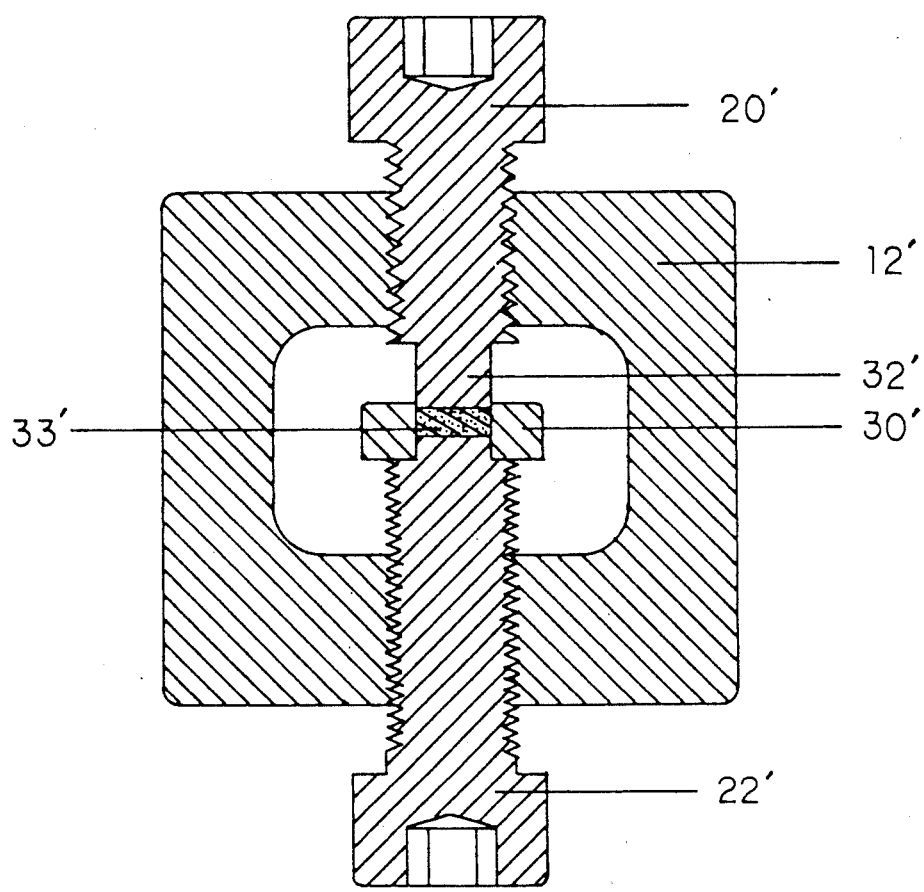
FIG. 3 is a view similar to FIG. 2 of another embodiment of the invention.

Referring now to FIG. 3 there is shown another embodiment of the present invention in which the upper bolt 20' and the lower bolt 22' are the same size, but have slightly different thread pitches. For instance, a 7/16 - 24 thread may be used in the top bore and a 7/16 - 28 in the bottom bore. A standard 7/16 - 14 top bore thread and a 7/16 - 20 bottom bore thread have also been found to be satisfactory. In this embodiment both bolts 20' and 22' are turned at the ends to form smooth pistons 32' and 34, respectively. Disc holder 30', is also formed with a smooth internal bore rather than a threaded bore to receive in a smooth tight fit the pistons 34 and 36.

As may be seen in FIG. 3, in operation the lower anvil 22' is threaded partway into the opening 14' of the vise 12' and the disc holder 30' is then placed over the end of the bolt 22' to sit on the shoulder formed by the piston 34 so as to form a dish or receptacle on the top of the anvil 22'. When anvil 20' is rotated down toward anvil 22', piston 32 will fit snugly within the holder 30' to form the press of the present invention. It also should be noted that the depth of the piston 32' on the anvil 20' is long enough so as to extend through the holder 30' so that if it is desired to remove the disc 33' from the holder 30' for any reason, that the holder 30' may be positioned about the anvil 20' and the holder held stationary and the anvil used as a plunger to gently eject the disc 33' from the holder 30'. The ejected disc 33' can then, of course, be encapsulated or otherwise prepared for further processing and analysis.

Figure 4:
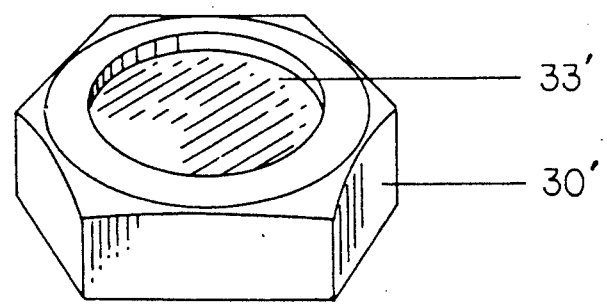
FIG. 4 is a perspective view of a disc holder for use with the embodiment of FIG. 3.

Referring now to FIG. 4 there is shown a perspective view of the holder 30' of the second embodiment of the present invention, in which is positioned a disc 33' of material for spectrographic analysis. The entire holder and disc may be placed in the sample mount or the disc 33' may be removed as indicated above for encapsulation or other processing.

Thus, a very simple and economical press for preparation of discs for spectrographic analysis is provided which can be quickly and easily used to provide a disc in a holder or to provide a disc separate from a holder, as desired, each with improved disc quality and surface smoothness.

In the foregoing embodiment bolts 20 and 22 have been shown as standard Allen head cap screws and the thread bores as being conventional right hand threads. It should be understood that other bolts could be used and that one bore could be a left hand thread with a left hand threaded bolt so that upon holding the bolts stationary and rotating the vise 12, the bolts would be brought together to compact material placed on the end of one.

While the invention has been described in the specification and illustrated in the drawings with reference to a preferred embodiment, it will be understood by those skilled in the art that various changes may be made and equivalents substituted for elements of the invention, without departing from the scope of the claims.

What is claimed is:

1. A screw thread press for forming sample discs for spectrographic analysis which comprises:
    a frame member having opposed sides and ends and having an opening through the center thereof;
    a first threaded hole in one side of said frame member extending to said center opening;
    a second threaded hole formed in the opposite side of said frame member in axial alignment with said first threaded hole and extending to said center opening;
    first and second anvil screw members rotatably mounted in said first and second threaded holes;
    means for holding said anvil screw members stationary when said frame member is rotated about said anvil screw members; and
    means for causing said anvil screws to come together when said frame member is rotated about said anvil screws.

2. A screw thread press as claimed in claim 1 wherein said first threaded hole and anvil screw have a different thread pitch than said second hole and anvil screw.

3. A screw thread press as claimed in claim 1 wherein said first anvil screw is larger in diameter and has a greater thread pitch than said second anvil screw.

4. A differential screw thread press as claimed in claim 1 further including a disc holder engaged on the end of one of said anvil screw members adapted to receive therein the end of the other said anvil screw member to compact sample material placed therein when said frame member is rotated.

5. A screw thread press as claimed in claim 4, wherein the end of one of said anvil screws is a smooth piston adapted to mate with a disc holder mounted on the end of said other anvil screw.

6. A screw thread press as claimed in claim 1 wherein said means for holding said anvil screw members stationary includes an Allen wrench socket in the head of each anvil screw and a pair of long handle Allen wrenches adapted to fit in said Allen wrench sockets, said wrenches being formed so as to be gripped in one hand and held stationary relative to rotation of said frame member.

7. A screw thread press as claimed in claim 1 wherein said first threaded hole and first anvil screw are right hand threaded and said second threaded hole and second anvil screw are left hand threaded.

8. A screw thread press as claimed in claim 2 wherein said first and second threaded holes are threaded in the same direction so as to advance a screw axially therethrough 9. In a screw thread press for forming sample discs for spectrographic analysis, the method of forming smooth surface discs which comprises:
    providing a vise having therein a pair of spaced apart axially aligned threaded holes having different thread pitches;
    positioning a first threaded anvil screw in one of said holes;
    placing a quantity of material to be compacted on the end of said first anvil screw positioned in said frame;
    positioning a second anvil screw in said other hole with the end thereof in close juxtaposition to the material on the end of said first anvil screw;
    holding said first and second anvil screws stationary;
    rotating said frame about said anvil screws to cause them to come together so as to compact the material to be compacted into a solid disc having smooth flat surfaces without any relative rotary motion marks.

10. In a differential screw thread press for forming sample discs for spectrographic analysis, the method of forming smooth surface discs which comprises:
    adjusting a first threaded screw in a frame;
    mounting a material holder on the end of said first threaded screw;
    placing a quantity of material to be examined in said holder;
    adjusting a second threaded screw positioned in axial alignment with said first screw in the frame until it just touches the other side of said material in said holder;
    holding said first and second threaded screws from rotation;
    rotating the frame about said threaded screws to force them together to compact said material into a solid disc.

* * * * *